United States Patent [19]
Kühne

[11] Patent Number: 5,741,272
[45] Date of Patent: Apr. 21, 1998

[54] APPARATUS FOR THE FRAGMENTATION OF CONCRETIONS IN THE MEDICAL FIELD

[76] Inventor: Udo Kühne, Kanderstegstrasse 22, CH-3714 Frutigen, Switzerland

[21] Appl. No.: 585,301

[22] Filed: Jan. 11, 1996

[30] Foreign Application Priority Data

Jan. 13, 1995 [DE] Germany .................. 195 00 893.6

[51] Int. Cl.⁶ .................................................. A61B 17/22
[52] U.S. Cl. ............................ 606/128; 604/22; 606/127
[58] Field of Search ........................ 606/107, 127, 606/128, 167, 19, 22, 902, 170, 171, 184, 185

[56] References Cited

U.S. PATENT DOCUMENTS 3,990,453 11/1976 Douvas et al. ...................... 606/107
3,994,297 11/1976 Kopf ................................... 606/107

*Primary Examiner*—Glenn Dawson

[57] ABSTRACT

A lithotripter for fragmenting concretions has a hollow probe with a first end that is arranged to face a concretion to be fragmented, and a second end that is received by a housing. A drive arrangement is arranged in the housing and produces energy and/or impulses at the second end of the hollow probe. The hollow probe has a lateral outlet opening and is surrounded by a connecting device to which a suction tube is attached, so that aspiration of fragmented concretions takes place outside the housing.

40 Claims, 1 Drawing Sheet

APPARATUS FOR THE FRAGMENTATION OF CONCRETIONS IN THE MEDICAL FIELD

BACKGROUND OF THE INVENTION

1. Field of the Invention

The invention relates to an apparatus for the fragmentation of concretions in the medical field.

2. Discussion of Prior Art

Such an apparatus, known as an ultrasonic shock wave lithotripter, is known from German Laid-Open Patent Application DE-OS 22 56 127. This apparatus has a probe constructed as a suction tube and driven by a transducer in order to fragment urinary or renal calculi. During the fragmentation process, the fragments of the concretions are aspirated by means of the suction tube and through the transducer by means of a suction connection connected to the end of the transducer.

This apparatus has the disadvantage of an expensive construction and arrangement because of the central aspiration which takes place through the drive of the suction tube. Such a central aspiration is only possible with a piezoelectric transducer such as is provided with this apparatus. Such a central aspiration with a hollow probe is excluded, for example, in the case of pneumatic, electrokinetic and electrohydraulic drives for the production of ultrasonic shock waves, since a mass body has to strike the input boundary surface, arranged in a housing, of a shock wire.

SUMMARY OF THE INVENTION

The invention has as its object to provide an apparatus of the above-mentioned kind, in which an aspiration of the fragmented concretions through a hollow probe is made possible, independently of the kind of driving of the apparatus.

This object is attained by an apparatus having a housing, a hollow probe having a first end arranged to face a concretion to be fragmented and a second end received by the housing, and a drive arrangement arranged in the housing for producing and conducting energy to the second end of the hollow probe, wherein the hollow probe has at least one lateral outlet opening.

The at least one outlet opening, arranged laterally on the hollow probe, makes it possible for an aspiration of the fragmented concretions to take place outside the housing of a lithotripter. The kind of driving can thereby be freely selectable. For example, an electrohydraulic, electrokinematic, or electro-pneumatic drive, or a drive by means of an ultrasonic transducer, such as for example a piezoelectric element, can take place. By this means, and particularly in the case of the last-named kind of driving, a design of the drive in the housing can be given which is constructionally relatively simple.

The lateral aspiration further permits the provision of simpler manipulation of such a lithotripter, since this hollow probe has a diameter which corresponds to the otherwise known probes and thus can be introduced with relative ease into the urinary ducts. Moreover, a constant pressure can be built up by aspiration into a hollow probe, and makes possible effective and controllable aspiration.

Additionally, the invention includes the following advantageous features.

The outlet opening is relatively remote from the end of the hollow probe which faces towards the concretion to be fragmented. In this manner, the small diameter of the hollow probe can be kept small over the whole section of the hollow probe which is to be introduced into the ureter. Moreover, the free length of the hollow probe which can be introduced into the human body is not impeded by further constructional elements required for the aspiration of the fragmented concretions.

A connecting device surrounds the lateral outlet opening and a suction tube is connected to the connecting device. This enables the liquid and fragments that emerge from the laterally arranged outlet opening to be conducted over by means of a connecting device into an aspiration tube and transported away. A simple and cost-effective arrangement is provided by this connecting device which surrounds the outlet opening and with which an aspiration of the fragmented concretions outside the housing of the lithotripter can take place. This connecting device forms an aspiration coupling between the outlet opening and the aspiration tube.

The connecting device includes a connecting body and a connecting sleeve arranged rotatably on the connecting body to which the suction tube is connected. This makes an easy handling of the lithotripter possible with at least one aspiration function with a connecting device arranged to the hollow probe. By means of the freely rotatable arrangement of the aspiration tube with respect to the connecting device, or with respect to the hollow probe, the aspiration tube can always be arranged in an optimum position with respect to the housing of the lithotripter. A special manipulation or care during use of the lithotripter in order to prevent blocking because of a particular position of the tube can be thereby excluded. The aspiration tube can right itself, due to the freely rotatable arrangement, without a special manipulation being necessary for this purpose.

The hollow probe is arranged to be freely rotatable and at least partially axially movable with respect to the housing by means of the connecting body. This makes it possible to avoid impairing the hollow probe in its functioning and/or operation. Energy and/or impulses are introduced by the respective drive into the hollow probe at its end facing towards the drive, and are conducted through the hollow probe to the concretion which is to be fragmented. Translational motions and vibrations in a wide frequency spectrum occur. Because of this preferred arrangement, the hollow probe does not encounter any impairment, so that the energy and/or impulses that are produced can be transmitted substantially without losses to the tip of the probe and can lead to an efficient fragmentation of the concretions.

A plurality of sealing elements surround the lateral outlet opening. The sealing elements comprise sealing rings positioned respectively in front of and behind the lateral outlet opening seen in the axial direction of the hollow probe. This can provide a liquid-tight connection of the hollow probe to the connecting device. Moreover an aspiration can be produced that can work at a high pressure. Simple O-rings can be used as sealing elements for this purpose, and, being mass-produced articles, are favorable in cost.

The hollow probe has a pair of flanges having a diameter enlarged with respect to the hollow probe by means of which the sealing elements are guided between them with lateral play. The sealing elements are arranged to close the connecting device liquid tight with respect to the lateral outlet opening. This enables the sealing rings to be positioned in a defined position relative to the at least one outlet opening, and able to form a secure seal to the connecting body of the connecting device.

At the same time, the sealing rings can be kept in position by the flanges during the fitting of the connecting device, and can ensure that the outlet opening remains free. Preferably only one sealing ring is arranged between the flanges, which are spaced apart and mutually parallel; the lateral play of the sealing rings makes it possible for the hollow probe to be axially movable relative to the connecting device, at least to the extent that the energy and/or impulses can be transmitted to the hollow probe tip without being reduced.

The hollow probe has a flat floor between at least one pair of flanges. The sealing element lies in linear contact with the flat floor, with slight pre-stress with respect to the pair of flanges. The flat floor has a finely machined surface and the sealing element is of wear resistant construction. Because of these features, the connecting device can be attachable to the hollow probe liquid-tightly and for a long period, and can make possible a long duration of operation.

Two pairs of flanges are provided on the hollow probe, and two sealing elements are positioned respectively between these pairs of flanges and the connecting body. The connecting body has a first bore that in a mounted state of the connecting body cooperates with the two sealing elements to form a first flushing chamber. The first flushing chamber is constructed between the output opening and the connecting body, surrounding the hollow probe, and bounded by the flanges arranged to the left and right of the outlet opening. This makes it possible for an aspiration of the fragmented concretions to take place independently of the radial positioning of the outlet opening relative to the connecting body, since the flushing chamber is constructed as an annular chamber. This makes possible a simple and positive handling of the connecting device when it is mounted to the hollow probe, since the alignment of the outlet opening of the hollow probe can be optional.

The first bore has an annular section substantially located opposite the lateral outlet opening, and has an enlarged diameter with respect to other sections of the first bore. This arrangement is favorable to flow, for making possible the rapid and trouble-free aspiration of liquid and fragmented concretions. Moreover, this arrangement is free from undercuts that could result in an accumulation of centered concretions and, with an increasing operating period, could also result in a displacement of the opening.

The connecting body has a second bore adjoining the first bore, through which the hollow probe passes. The second bore provides a guide section for the hollow probe. This ensures that the hollow probe can additionally be guided by means of the second bore. The length of the second bore is variable according to requirements, so that kinking and damage of the hollow probe can be reduced.

The first end of the hollow probe can be introduced into the first bore for mounting of the hollow probe. The first end of the hollow probe can pass through the second bore. A flange that is located first in the direction of assembly of the connecting body to the housing forms a pre-centering means. This makes a simple mounting of the connecting body on the hollow probe possible. The hollow probe can first be introduced into the first bore and then passed through the second bore, so that the first bore, after a further guiding of the hollow probe through a first flange which faces the first bore, can be pre-centered, which facilitates a subsequent pushing of the connecting device as far as the mounting end position.

The connecting body has at least one passage opening that is connected to the first flushing chamber. The second flushing chamber is connected to the passage opening, and is formed between the connecting body and the connecting sleeve. This enables the connecting sleeve to be positioned in an optional position relative to the connecting body. Here, a second flushing chamber is formed between the connecting body and the connecting sleeve, and similarly to the first flushing chamber makes an aspiration independently of the position of the passage opening relative to the connecting sleeve possible, since the flushing chamber is constructed as a through annular chamber.

At least one connecting pipe is removably connected with respect to the connecting sleeve. The connecting pipe receives the suction tube. This enables different pipe connections to be arranged in order for the reception of suction tubes having different diameters, and hence in through flow amount, depending on the amount to be aspirated. Several passage openings can be provided in the connecting sleeve for this purpose.

At least one sealing element surrounds the passage opening and is arranged between the connecting body and the connecting sleeve. Left and right of the passage opening, the connecting body has a flange pair that respectively receives a sealing element. The sealing element is a sealing ring guided with lateral play in the flange pair. The size of the first and second flushing chambers is determined by the size of the flanges facing towards the lateral opening and the passage opening. This enables radially free movement of the connecting sleeve relative to the connecting body. The suction tube can thereby have a direct feed to the connecting device, which is thus free from twisting relative to the lithotripter. The arrangement of the connecting sleeve relative to the connecting body has the same arrangement as the hollow probe relative to the connecting body, and thereby shares the same advantages.

The flanges of the hollow probe are constructed as compression supports for the connecting body, and the flanges of the connecting body are constructed as compression supports for the connecting sleeve. This provides a stable arrangement between the hollow probe and the connecting body, or between the connecting body and the connecting sleeve. Preferably, these flanges have flat end faces, so that on compression of the sealing rings, the envelope inner surface of the connecting body or connecting sleeve can come to be adjacent to the end faces of the flanges of the hollow probe or of the connecting body. For compression support, the bores of the connecting body and the connecting sleeve can be reinforced.

At the end of the connecting body facing towards the housing, the connecting body has a fastening element that is constructed as an internal thread. The connecting body has an outer periphery with an irregular surface that faces towards the first end of the hollow probe, and has a larger diameter than other portions of the connecting body. This provides a simple design for fixing the connecting body to the housing. This advantageous one-piece construction makes it possible for the connecting body to be produced as an injection molded part that has at one end a screw thread which can be installed on a threaded pipe connection of the housing. For simple mounting or for simple screwing and unscrewing of the connecting body, an annular section with a large outer diameter is provided at the opposite end, and has on its outer surface a knurling or ribbing for better manipulation during mounting. As an alternative, the connecting body can be constructed in several parts, so that an arrangement corresponding to the connecting body can be provided by the cooperative action of several components.

The connecting sleeve is symmetrically constructed and has lead-in tapers. This simplifies manipulation of the connecting devices because on the one hand the leading tapers facilitate attaching the connecting sleeve to the connecting body. On the other hand, due to its symmetrical construction, the connecting sleeve can always be attached to the connecting body to function correctly, independent of the alignment of the connecting sleeve.

The connecting sleeve has an inner surface with a constant internal diameter. At least in its mounted state, the connecting sleeve is located opposite the flanges of the connecting body. This provides a simple embodiment of the connecting sleeve. It provides a defined abutment surface for the sealing elements that are guided by the flanges of the connecting body, to provide a liquid-tight arrangement with a closed flushing chamber and to maintain the symmetry.

The connecting device is constructed of plastic. This enables the device to be easily dismantled and sterilized after each use. In particular, a higher degree of cleanliness of the hollow probe and also of the connecting device is made possible by the design, free from undercuts, of the connecting device. For this purpose, a "Peek" plastic, which is particularly suitable for sterilization in autoclaves, can be used.

The hollow probe comprises a probe foot, a tube, and a hollow probe tip. The probe foot and the hollow probe tip are soldered to the tube. This makes possible simple production of hollow probes at a favorable cost. By means of the construction of the hollow probe in several parts, with a probe foot, a tube, and a hollow probe tip, simple workpiece geometries can be provided which can be produced at a favorable cost and which can be assembled into a hollow probe. The parts can be firmly connected together by a simple cold or hot soldering.

The tube is inserted in a blind bore in the probe foot and the lateral outlet opening is formed in the tube after the tube is soldered to the probe foot. This enables the tube to be securely and stably received by the blind bore. Moreover, by the insertion of the tube into the probe foot and by the formation of the lateral outlet opening in the tube after the tube has been soldered in, an arrangement which is free from undercuts is provided in the blind bore of the probe foot. By means of different bore diameters of the blind bore, the probe foot can be matched to the respective tube diameter.

The probe foot has a probe foot end arranged in a guide section of the housing, a flushing chamber section adjoining the probe foot end and at least one outlet opening that merges into an end section of the probe foot. This makes possible the embodiment of the probe foot as a rotary part. Moreover the probe feet with these features can be sold as spare parts.

The hollow probe tip has a sharp-edged end arranged to face a concretion that is to be fragmented. This provides a simple and cost-effective embodiment of a probe tip, which is also interchangeable as a unit after long use, while the tube and the probe foot can continue to be used.

The hollow probe tip is a rotary part. This ensures that the energy and/or impulses introduced at the second end of the hollow probe, that is, at the end of the probe foot which faces towards the drive device, can be transmitted substantially without loss to the end of the hollow probe which faces the concretion.

The probe foot has an operating cross section that is larger than the operating cross section of the tube. This ensures that the successive cross sections or openings are enlarged in the aspiration direction or in the flow direction of the liquid, so that an arrangement free from undercuts is provided from the inlet opening of the probe tip as far as the aspiration tube. Furthermore, obstruction by deposits formed in cross sectional openings can be avoided.

The hollow probe tip has an inlet opening having a cross section constructed increasingly larger over the lateral outlet opening of the hollow probe, and the passage opening of the connecting body is connected to at least one through bore of the connecting sleeve. This enables a higher degree of aspiration to be attained, which can be required when large shock wire diameters are used.

The hollow probe has at least one additional lateral outlet opening that can be arranged radially and/or axially of the first lateral outlet opening. Damping means are arranged between a stop of the connecting body formed by the first bore and the second bore, and a left-hand flange of the hollow probe seen in an axial direction of the connecting body. The right-hand flange of the hollow probe is constructed as a stop. It abuts an end-face of a threaded connecting pipe of the housing and forms an initial position into which the hollow probe automatically returns after each introduction of energy. These features enable the shock wire to be arranged in the housing with prestressing. The shock wire can thereby return to its initial position after each introduction of impulses or energy, so that the same conditions, and also a predetermined shock characteristic during the whole operation, can be provided for the production and transmission of energy and/or impulses.

DESCRIPTION OF THE DRAWING

The invention will now be described with reference to a preferred embodiment, in which

FIG. 1 a schematic sectional representation of a device according to the invention for the fragmenting of concretions.

DETAILED DESCRIPTION OF A PREFERRED EMBODIMENT

Figure 1:
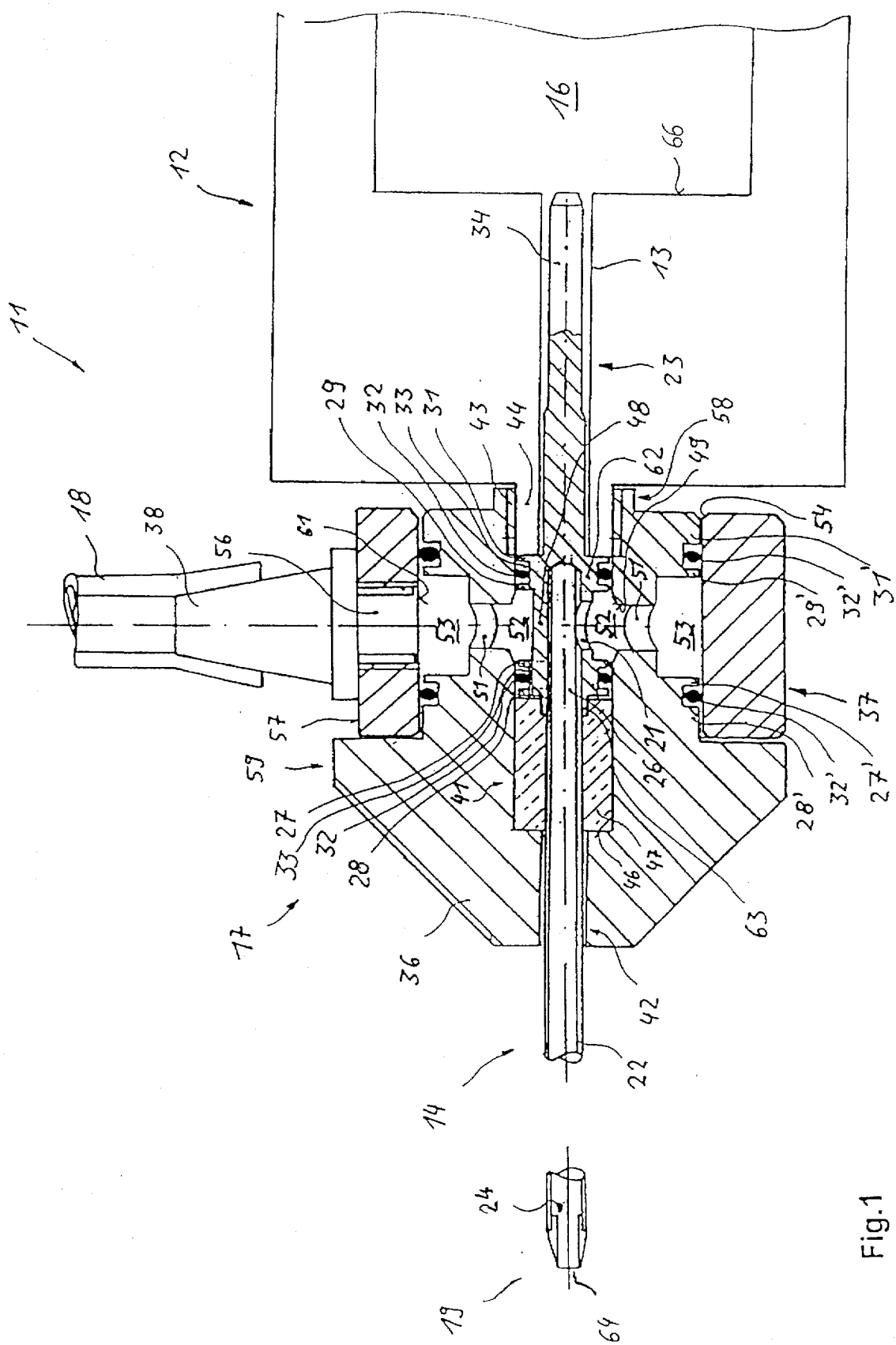
FIG. 1 shows.

A schematic representation of a device 11 for the fragmentation of concretions, for example, bladder or kidney stones, or the like, is shown in FIG. 1. The apparatus 11 has a housing 12 which receives a hollow probe 14 in a guide section 13. A drive arrangement 16 is provided in the housing 12, and can be constructed as, for example, a pneumatic, electrohydraulic or electro-kinematic drive. An ultrasonic transducer, such as, for example, a piezoelectric transducer or the like, can also be provided. Furthermore, alternatives to the aforementioned kinds of drives can be provided which can effect the introduction of energy and/or impulses to the end of the hollow probe 14 facing towards the drive arrangement 16.

The apparatus 11 known as a lithotripter furthermore has a connecting device 17 which is connected to the housing 12 and surrounds the hollow probe 14, and to which a suction tube 18 can be connected. During the use of the apparatus, a fragmentation of the concretions takes place due to the action of a hollow probe tip 19; the fragments are sucked out through the hollow probe 14, and are fed via the connecting device 17 to the suction tube 18, by which they are conducted away.

An arrangement is provided according to the invention by an outlet opening 21 which is arranged laterally on the hollow probe 14 and lies outside the housing 12, and with the connecting device 17 which can be connected to the suction tube 18; this arrangement makes possible the aspiration, which takes place outside the housing 12 and the drive arrangement 16 arranged therein, of fragmented concretions by means of a hollow probe 14. The connecting device 17 thus forms a suction coupling between the free section of the hollow probe 14 lying outside the housing 12 and the suction tube 18.

The hollow probe 14 consists of a tube 22, a probe foot 23, and the hollow probe tip 19. These three components 19, 22, 23 can advantageously be inserted one into the other, and are fastened together by a soldered connection. A hollow probe 14 which is free from undercuts can be provided in this manner.

The hollow probe is constructed as a rotary part and is constructed with a sharp-edged end 24 facing towards the concretion to be fragmented. The size of the inlet opening of the hollow probe tip 19 determines the size of the fragmented concretions which it is possible to transport away. The hollow probe tip 19 has a shoulder at an end 24 of the hollow probe tip 19 facing towards the hollow probe 14, so that the tube 22 of the hollow probe 14 can be attached to the shoulder of the hollow probe tip 19. It is thereby ensured that no undercut, but an enlargement of the cross section, is present in the flow direction.

The tube 22 can be made to a length specific to the application and has a constant cross section. It can be provided that the tube 22 is widened out from the hollow probe tip 19 to the probe foot 23. Blocking up of the hollow probe 14 can thereby be avoided, and moreover a higher stability can be attained.

The tube 22 can be inserted into a blind bore 26 of the probe foot 23. The blind bore 26 has a depth of at least 1 cm, so that guiding of the tube 22 in the blind bore 26 is effected. A rigid and secure retention can thus be effected. After the tube 22 has been soldered into the blind hole 26 of the probe foot 23, the outlet opening 21 is drilled in the tube 22, so that the medium to be transported away can come out through the interior of the hollow probe 14 via the outlet opening 21. The probe foot can have, at its left-hand end, an end section 63 so that the guide surface of the tube 22 can be increased.

The probe foot 23 has a left and a right flange 27 and 29, equispaced from the outlet opening. Respectively parallel to these and spaced outwardly from them, forming a U-shaped recess, are a further left-hand flange 28 and a further right-hand flange 31. The left-hand flange pair 27, 28 and right-hand flange pair 29 31 which are thereby formed each receive a sealing element 32 which consists of an O-ring. Two or more O-rings can also be arranged between a respective flange pair, 27, 28 and 29, 31. The flanges 27, 28 and 29, 31 are spaced apart parallel to each other such that the seal 32 arranged between them has a lateral play. Crushing of the seals 32 when a connecting body 36 of the connecting body 17 is put in place can thereby be avoided by a lateral rolling away. The seals 32 lie under slight prestress on a respective floor 33 arranged between the left-hand pair 27, 28 of flanges and between the right-hand pair of flanges 29, 31. Each floor 33 has a slight surface roughness due to a fine machining, resulting in a longer life of the seals 32. The seals 32 are preferably made of a wear-resistant, elastic material.

A substantially cylindrical probe foot end 34 is provided adjoining the right-hand flange pair 29, 31, and has a full cross section. The surface of the full cross section is larger than the cross sectional surface of the tube 22, whereby it is ensured that the energy and/or impulses transmitted to the probe foot end 34 can be transmitted nearly without loss to the hollow probe tip 19.

The connecting device 17 consists of the connecting body 36 and a connecting sleeve 37, on which is arranged a connecting pipe 38 to receive the suction tube 18. The connecting body 36 is advantageously made in one piece, and has a first, central bore 41 which merges into a second bore 42 of smaller diameter. The second bore 42 is advantageously made longer, so that guiding of the hollow probe is provided which is additional to the guiding of the hollow probe 14 in the blind bore 26. The first bore 41 substantially surrounds the outlet opening 21 with the flange pairs 27, 28 and 29, 31 spaced to the left and right of it. An internal thread 43 is provided on the end of the connecting body 36 facing towards the housing 12, and a threaded pipe connection 44 of the housing 12 can be fastened to it.

The hollow probe 14 can be attached to the housing 12 under a prestress by means of the connecting body 36. A stop surface 46 is formed between the first and second bores 41, 42; a damping means 47 abuts it on one side and is supported on the other side on the left-hand flange 28. The damping means 47 consists, for example, of a rubber-elastic tubular piece and is pushed onto the hollow probe. It can also be provided that a spring, or laminated springs, or otherwise elastic material, is provided as the damping element.

The degree of prestress, or the possible freedom of movement, can be determined, at least in the axial direction of the probe, by the length of the damping means 47 and the choice of its material. By the screwing of the connecting body 36 on the threaded pipe connection 44, and due to the arrangement of the damping medium 47, the right-hand flange 31 can come to abut against a preferably flat end face of the threaded pipe connection 44. On further screwing in, the damping means 47 is prestressed, so that the hollow probe 14 can always be pulled back into an initial position as shown in FIG. 1, in which the right-hand flange 31 abuts against the end face of the threaded pipe connection The length of the probe foot end 34, which is arranged and guided in the guide section 13, can be constructed, in dependence on the kind of operation, to be more or less projecting from the guide section 13, or ending within this, or flush with an adjacent surface 66 in the housing 12.

To fasten the hollow probe 14 on the housing 12, the connecting body 36 can be pushed onto the hollow probe 14 from the left, so that the hollow probe tip 19 is passed first through the first bore 41 and then through the second bore 42, until the first bore 41 is first pre-centered, by means of the damping means, to be pushed on further. A further pre-centering by the left-hand flange 28, which can advantageously have a lead-in taper to make it easier to push the connecting body 36 on, takes place when the latter is further pushed on. The internal diameter of the first bore is advantageously constant in this region, so that easy pushing on is facilitated. The seals 32 in the mounted state abut the outside surface of the first bore 41 under low stress. The lateral play of the seals 32 relative to the flange pairs 27, 28 and 29, 31, and also the small stress acting on the seals 32 in the mounted state, make it possible for the hollow probe 14 to be movable without losses of energy and/or impulses in the axial direction with respect to the connecting body 36, which is arranged fixed to the housing 12. At the same time, by this advantageous arrangement, the hollow probe 14 can be received, for radial free rotation, by the connecting body 36.

The flange pairs 27, 28 and 29, 31 respectively have only a slightly smaller diameter than the first bore 41, so that the end faces of the flanges 27, 28 and 29, 31 can lie against the outer surface of the first bore 41 and provide a protection against compression by forces which act on the hollow probe 14 and/or the connecting body 36.

The first bore 41 has an enlarged annular section 49 which, in the mounted state of the connecting body, is arranged between the flange pairs 27, 28 and 29, 31. At least one passage opening 51, and advantageously two, passage openings 51 are provided, and are advantageously aligned in the radial direction to the outlet opening 21.

A first flushing chamber 52 is formed by the left-hand flange 27, right-hand flange 29, and a pipe section 48, which form a flushing chamber 62 of the probe for 23, and the annular section 49 of the first bore 41. This forms a cavity completely surrounding the outlet opening 21. This makes it possible for aspiration to be effected, because of the first flushing chamber 52 which completely surrounds the pipe section 48, independently of the alignment of the outlet opening 21 with respect to the through flow opening 51. The passage opening 51 is furthermore made larger than the outlet opening 21. Moreover the enlarged annular section 49 preferably has a transitional taper with respect to the first bore 41, so that the first flushing chamber 52 is free from undercuts and is favorable for flow.

The passage openings 51 connect the first flushing chamber 52 to a second flushing chamber 53, which is formed by the connecting body 36 and a connecting sleeve 37 which can be attached to the connecting body 36. The construction of the second flushing chamber corresponds in principle to the embodiment of the first flushing chamber 52. Likewise a left-hand flange pair 27', 28' and a right-hand flange pair 29', 31' are provided, which receive a respective seal 32'. The connecting sleeve 37 is likewise arranged freely with its inner surface 61 rotatable with respect to the connecting body 36 and likewise axially movable to a small degree, so that aspiration is effected independently of the position of at least one through bore 56.

The connecting sleeve 37 is constructed symmetrically as a wide ring, and has insertion bevels 54 so that easy attachment of the connecting sleeve 37 to the connecting body 36 is made possible.

A through bore 56, into which a connecting pipe 38 can be screwed, is provided in the connection sleeve 37. Several connecting pipes 38 for aspiration can also be provided on the connecting sleeve. A flat 57 is provided on an external periphery of the connecting body 37, so that the connecting pipe 38 has a defined abutment face for its attachment and can be securely fastened.

The connecting sleeve 37 is bounded in its axial direction of motion by the connecting body 36 to the left and by the housing 12 to the right, in the mounted state. A connecting pipe 58 which has the inner thread 43 of the connecting body 36 is made small, so that the spacing between the housing 12 and the end face of the connecting sleeve which faces towards the housing 12 is made small, and even in an extreme position of the connecting sleeve, at least the left-hand flange 28' or the right-hand flange 31p remains covered.

The through bore 56 is made enlarged with respect to the passage opening 51, so that an arrangement which is favorable for flow and is free from undercuts is again provided.

The connecting body 36 has an external circumference 59, which is provided with knurling or fluting at the end of the connecting body opposite to the pipe connection 58, in order to make possible an easy rotation up and down of the connecting body 36 on the threaded connecting pipe 44 of the housing 12. This is of particular importance, since a cleaning and sterilization of the hollow probe 14, the connecting device 17, and the housing is necessary after each use of the lithotripter. The wear-resistant seals 32, 32' can be changed after, for example, twenty to thirty uses of the lithotripter, in order to be able to maintain a high degree of aspiration, since otherwise outside air could be drawn in, or the connecting device 17 would have unsealed places.

The connecting device 17, or the suction coupling between the hollow probe 14 and the suction tube 18 substantially consists of three simple parts 36, 37, 38 which can be mounted and dismantled, and which are all similarly free from undercuts in their construction, so that they can easily be demounted from the housing 12 with the hollow probe 14 and dismantled into individual parts so that these can be individually placed in an autoclave for sterilization. The connecting device 17 is advantageously made of a plastic which can be autoclaved, preferably a "Peek" material. Other plastics can also be used which are sterilizable and at the same time dimensionally stable.

The hollow probe can consist of chrome-nickel steel, special steel, or similar steels which are suitable for use in medical technology. The tube 22 can consist, for its reinforcement, of a drawn wire or wrought wire.

The arrangement of the connecting device 17 to the housing 12 and the hollow probe 14 arranged therein have no action, which for example might have a damping effect, on the transmission of the energy and/or impulses introduced into the probe foot end 34. By the advantageous arrangement of the sealing elements 32 between the flange pairs 27, 28 and 29, 31 of the first bore 41, the hollow probe 14 remains de coupled from the connecting body 36 and thus from the connecting device 17. The spring force of the damping means 37, acting on the left-hand flange 28, is also provided in a similar form in a conventional and known arrangement of the hollow probe to the housing 12. This prestressing effects a certain impact characteristic and needs to be balanced, so that unbraked energy and/or impulse transmission to the hollow probe tip 19 can be provided.

An advantageous alternative embodiment of a connecting device 17 for the aspiration of fragmented concretions is such that the connecting device 17 is arranged separately from the housing 12, that is, the connecting device 17 would not be arranged with the housing 12 by means of a screw connection. For this purpose, an additional cap nut can be provided, which fastens the hollow probe 14 to the housing 12. The connecting device 17 can surround the outlet opening 21 of the hollow probe 14 at a small spacing from this hollow probe, and can be arranged stationary to this in the operating state, and can be substantially identical to the embodiment described in FIG. 1.

Advantageously, a one-piece embodiment of the connecting device can also be possible with an arrangement of the connecting device which is separate from the housing, since the connecting device itself can be arranged to be freely rotatable with respect to the hollow probe.

A further advantageous alternative embodiment consists in that the connecting device consists of elastic material and simultaneously forms a seal to the hollow probe. This elastic connecting device likewise has a flushing chamber which surrounds the outlet opening, so that the connecting device can be positionable independently of the arrangement of the outlet opening. For this purpose, the damping means can be formed at the same time by the elastic embodiment of the connecting device, and can effect a return of the hollow probe to an initial position after the introduction of the energy and/or impulses to the second hollow probe end.

By means of this advantageous embodiment, the connecting device can be arranged to be freely rotatable relative to the outlet opening of the hollow probe, and the impact characteristic can still be retained, due to the axially movable mounting of the connecting device with respect to the hollow probe.

I claim:

1. An apparatus for fragmentation of concretions comprising:
   a housing (12),
   a hollow prove (14) having a first end arranged to face a concretion to be fragmented and a second end received by said housing,
   a drive arrangement (16) arranged in said housing for producing and conducting energy to said second end of said hollow probe, wherein said hollow probe has at least one lateral outlet opening (21), said at least one lateral outlet opening (21) being spaced at a distance from said first end of said hollow probe,
   a connecting device (17) surrounding said at least one lateral outlet opening, and
   a suction tube (18),
   said connecting device (17) comprising a connecting body (36) and a connecting sleeve (37) arranged rotatably on said connecting body (36) to which said suction tube (18) is connected.

2. The apparatus according to claim 1, wherein said hollow probe is arranged to be freely rotatable and at least partially axially movable with respect to said housing by means of said connecting device.

3. The apparatus according to claim 1, further comprising at least one sealing element (32) arranged within said connecting device (17) and surrounding said at least one lateral outlet opening.

4. The apparatus according to claim 3, wherein said sealing element is of a wear resistant construction.

5. The apparatus according to claim 1, further comprising a plurality of sealing elements (38) comprising sealing rings (32) arranged within said connecting device (17) and positioned respectively in front of and behind said at least one lateral outlet opening, seen in an axial direction of said hollow probe.

6. The apparatus according to claim 1, further comprising at least one sealing element (32), wherein said hollow probe has at least one flange (27, 28) having a diameter enlarged with respect to said first and second ends of said hollow probe for guiding said at least one sealing element.

7. The apparatus according to claim 6, wherein said hollow probe has at least one pair of flanges (27, 28) for receiving and guiding said at least one sealing element there between with lateral play.

8. The apparatus according to claim 7, wherein said hollow probe has two of said sealing elements (32) guided by two of said pair of flanges (27, 28, 29, 31) positioned respectively in front of and behind said at least one lateral outlet opening, seen in an axial direction of the hollow probe, which sealing elements are arranged to close said connecting device liquid tight with respect to said at least one lateral outlet opening.

9. The apparatus according to claim 8, wherein said flanges (27, 28, 29, 31) of said hollow probe (14) are constructed as compression supports for said connecting body (36).

10. The apparatus according to claim 7, wherein said hollow probe has a flat floor (33) between said at least one pair of flanges, on which said sealing element lies in linear contact.

11. The apparatus according to claim 10, wherein said flat floor has a finely machined surface.

12. The apparatus according to claim 7, wherein said at least one sealing element is arranged with slight prestress with respect to said at least one pair of flanges.

13. The apparatus according to claim 1, further comprising two pairs of flanges (27, 28, 29, 31) on said hollow probe, at least two sealing elements (32) positioned respectively between said two pairs of flanges wherein said connecting body (36) has a first bore (41) that cooperates with said at least two sealing elements to form a first flushing chamber (52).

14. The apparatus according to claim 13, wherein said first bore has an annular section (49) substantially located opposite from said at least one lateral outlet opening, having an enlarged diameter with respect to other sections of said first bore.

15. The apparatus according to claim 13, wherein said connecting body has a second bore (42) adjoining said first bore, through which said hollow probe passes, said second bore providing a guide section for said hollow probe.

16. The apparatus according to claim 15, wherein said first end of said hollow probe is introduced into said first bore for mounting of said connecting body and passes through said second bore, whereby one of the flanges forms a pre-centering means.

17. The apparatus according to claim 1, wherein said connecting body (36) has at least one passage opening (51) that is connected to a first flushing chamber (52).

18. The apparatus according to claim 17, wherein at least one sealing element (32') surrounds said at least one passage opening (51) and is arranged between said connecting body (36) and said connecting sleeve (37).

19. The apparatus according to claim 18, wherein said connecting body (36) has, on both sides of said at least one passage opening (51) a flange pair (27'28' and 29'31') that respectively receives one of said at least one sealing element (32').

20. The apparatus according to claim 19, wherein said at least one sealing element (32') comprises a sealing ring guided with lateral play in each said flange pair (27'28' and 29' 31').

21. The apparatus according to claim 19, wherein said flanges (27', 28', 29', 31') of said connecting body (36) are constructed as compression supports for said connecting sleeve (37).

22. The apparatus according to claim 19, wherein said connecting sleeve (37) has an inner surface (61) which has a constant internal diameter and is located opposite said flanges (27', 28', 29', 31').

23. The apparatus according to claim 1, further comprising at least one connecting pipe (38) removably connected with respect to said connecting sleeve (37), which receives said suction tube (18).

24. The apparatus according to claim 1, wherein said connecting body (36) has a fastening element (43), which is constructed as an internal thread, at an end of said connecting body facing towards said housing (12).

25. The apparatus according to claim 1, wherein said connecting body (36) has an outer periphery (59) which is located towards said first end of said hollow probe (14) and is constructed with a larger diameter than other portions of said connecting body, and has an irregular surface thereon.

26. The apparatus according to claim 1, wherein said connecting sleeve (37) is symmetrically constructed.

27. The apparatus according to claim 26, wherein said connecting sleeve (37) has lead-in tapers (54).

28. The apparatus according to claim 1, wherein said connecting device (17) is constructed of plastic.

29. The apparatus according to claim 1, wherein said hollow probe (14) comprises a probe foot (23), a tube (22) and a hollow probe tip (19).

30. The apparatus according to claim 29, wherein said tube (22) is inserted in a blind bore (26) in said probe foot (23), and said at least one lateral outlet opening (21) is formed in said tube (22) with said hollow probe tip (19) and said probe foot (23) soldered thereto.

31. The apparatus according to claim 29, wherein said probe foot has a probe foot end (34) arranged in a guide section (13) of said housing (12) and said at least one outlet opening (21) merges into an end section (63) of said probe foot, and a flushing chamber (62) adjoins said probe foot end (34).

32. The apparatus according to claim 29, wherein said hollow probe tip (19) has a sharp-edged end arranged to face a concretion to be fragmented.

33. The apparatus according to claim 32, wherein said hollow probe tip is a rotary part relative to said connecting body.

34. The apparatus according to claim 29, wherein said probe foot has an operating cross section that is larger than an operating cross section of said tube (22).

35. The apparatus according to claim 29, wherein said hollow probe tip (19) has an inlet opening (64) having a cross section constructed increasingly larger in the direction of said at least one lateral outlet opening (21) of said hollow probe (14) and at least one passage opening (51) of said connecting body (36) is connected to at least one through bore (56) of said connecting sleeve (37).

36. The apparatus according to claim 1, wherein said hollow probe (14) has at least one further lateral outlet opening arranged radially and/or axially of said at least one lateral outlet opening (21).

37. The apparatus according to claim 1, further comprising a damping means (47) arranged between a stop (46) of said connecting body (36) formed by a first bore (41) and a second bore (42) in said connecting body, and a flange (28) of said hollow probe (14).

38. The apparatus according to claim 1, wherein a flange (31) of said hollow probe (14) is constructed as a stop, abuts an end face of a threaded connecting pipe (44) of said housing (12) and forms an initial position into which said hollow probe (14) automatically returns after said drive arrangement produces energy.

39. An apparatus for fragmentation of concretions comprising:
- a housing (12),
- a hollow probe (14) having a first end arranged to face a concretion to be fragmented and a second end received by said housing, and
- a drive arrangement (16) arranged in said housing for producing and conducting energy to said second end of said hollow probe, wherein said hollow probe has at least one lateral outlet opening (21), two pairs of flanges on said hollow probe, at least two sealing elements positioned respectively between said pairs of flanges and a connecting body having a first bore that in a mounted state of said connecting body cooperates with said at least two sealing elements to form a first flushing chamber,
- wherein said connecting body (36) has at least one passage opening (51) that is connected to said first flushing chamber (52), and a second flushing chamber (53) that is connected to said at least one passage opening (51) formed between said connecting body (36) and a connecting sleeve (37).

40. An apparatus for fragmentation of concretions comprising:
- a housing (12),
- a hollow probe (14) having a first end arranged to face a concretion to be fragmented and a second end received by said housing, and
- a drive arrangement (16) arranged in said housing for producing and conducting energy to said second end of said hollow probe, wherein said hollow probe has at least one lateral outlet opening (21),
- wherein said hollow probe (14) comprises a probe foot (23), a tube (22) and a hollow probe tip (19), and said probe foot (23) and said hollow probe tip (19) are soldered to said tube (22).

* * * * *